United States Patent [19]

Ross et al.

[11] Patent Number: 4,897,260

[45] Date of Patent: Jan. 30, 1990

[54] COMPOSITIONS THAT AFFECT SUPPRESSION OF CUTANEOUS DELAYED HYPERSENSITIVITY AND PRODUCTS INCLUDING SAME

[75] Inventors: Peter M. Ross, New York; H. Leon Bradlow, Holliswood, both of N.Y.

[73] Assignee: The Rockefeller University, New York, N.Y.

[21] Appl. No.: 161,743

[22] Filed: Feb. 29, 1988

Related U.S. Application Data

[63] Continuation-in-part of Ser. No. 53,379, May 22, 1987, which is a continuation-in-part of Ser. No. 30,764, Mar. 25, 1987.

[51] Int. Cl.⁴ .................... A61K 7/40; A61K 7/42; A61K 7/44; A61K 7/48
[52] U.S. Cl. ..................... 424/59; 252/106; 424/47; 424/60; 424/70; 514/885; 514/886; 514/887; 514/937; 514/938; 514/944; 514/945; 514/969; 514/847
[58] Field of Search .............. 514/861, 863, 847; 424/59

[56] References Cited

U.S. PATENT DOCUMENTS

| | | | |
|---|---|---|---|
| 4,427,670 | 1/1984 | Ofuchi et al. | 514/861 |
| 4,432,976 | 2/1984 | Annen et al. | 514/861 |
| 4,435,390 | 3/1984 | Annen et al. | 514/861 |
| 4,512,987 | 4/1985 | Schindlery | 514/861 |
| 4,610,978 | 9/1986 | Dikstein et al. | 514/861 |

OTHER PUBLICATIONS

Laurent et al, Chem. Abs., 1975, vol. 83, 164419h.
Laurent et al (I), Chem. Abst., 1974, vol. 81, p. 105817x.
Gorsline et al, Chem. Abst., 1985, vol. 102, 125, 758j.
Lowe, N. J., J. Invest. Dermatol., 77, 147–153 (1981).
Lowe, N. J., et al., Cancer Research, 42, 3941–3943 (1982).

*Primary Examiner*—Dale R. Ore
*Attorney, Agent, or Firm*—Klauber & Jackson

[57] ABSTRACT

Glucocorticoid carboxylic acid esters and topical compositions thereof are utilized in methods for modulating cutaneous delayed hypersensitivity. Formulations of the glucocorticoid carboxylic acid esters are disclosed including incorporation into percutaneous drug delivery devices.

2 Claims, 1 Drawing Sheet

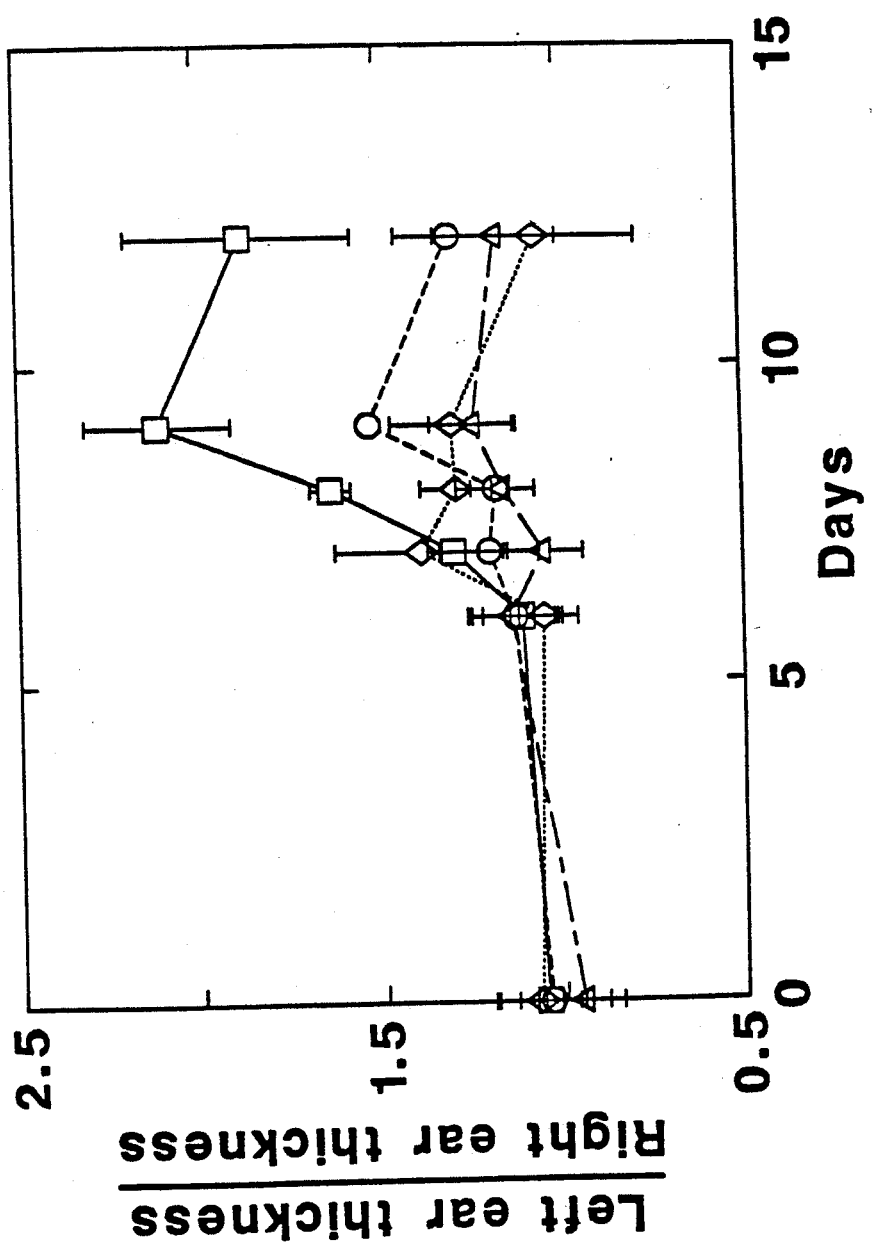

COMPOSITIONS THAT AFFECT SUPPRESSION OF CUTANEOUS DELAYED HYPERSENSITIVITY AND PRODUCTS INCLUDING SAME

RELATED APPLICATIONS

The present Application is a Continuation-In-Part of co-pending application Ser. No. 053,379, filed May 22, 1987, which is in turn a Continuation-In-Part of application Ser. No. 030,764, filed Mar. 25, 1987, by the inventors herein, and applicants claim the benefits of 35 U.S.C. §120 therefrom.

BACKGROUND OF THE INVENTION

The present invention relates generally to the modulation of cutaneous delayed hypersensitivity, and more particularly to compositions and products capable of such modulation, and their applications.

In general, the skin like the majority of the organs and tissues of the body, possesses a defensive mechanism responsive to invasive stimuli that are perceived to be harmful to normal functioning. Such mechanisms serve in most instances to localized cellular damage by isolating the situs of injury and attacking the manifestation of the invasive stimulus. The response known as delayed hypersensitivity that is exhibited by the skin is believed to be such a mechanism. As its name implies, delayed hypersensitivity represents a condition or state that the area of skin exposed to a harmful irritant will enter after a first uneventful exposure to the invasive stimulus or irritant. The manifestation of delayed hypersensitivity may include cellular swelling, heightened tactile discomfort, lesion-like eruptions and other such adverse conditions. For example, contact dermatitis occurs when the skin is exposed to a variety of harmful irritants.

Interestingly, certain harmful stimuli tend to suppress delayed hypersensitivity and in this sense, pose other dangers. For example, severe sunburn resulting from exposure to ultraviolet radiation has been found to suppress delayed hypersensitivity, as the expected rejection of the sunburned skin cells does not take place. In particular, the exposure to ultraviolet light which causes the sunburn likewise induces other changes in the skin which are believed to predispose, or lead, an individual to skin cancer. Such exposure can cause tumor graft tolerance and suppress delayed hypersensitivity (DH) [Parrish, J.A., ed. "The Effect of Ultraviolet Radiation on the Immune System", Johnson and Johnson Baby Products Company.]. Ultraviolet irradiation of mouse skin causes tolerance to the placing of relatively immunogenic skin tumor grafts. [Krinke, J. Nat. Cancer Inst. 57, pp. 211-215 (1976)]. The extent of suppression of delayed hypersensitivity (DH) by ultraviolet light has been used to quantify immunological tolerance caused by ultraviolet light, [Noonan, Springer Semin, Immunopathol., 4, pp. 293-304 (1981) and Parrish, cited above]. Irradiated mouse skin secretes low molecular weight protein that stimulates suppressor T cells in the spleen [Swartz, J. Invest. Dermatol. 83, pp. 305-307 (1984) and Schwartz et al., J. Invest. Dermatol., 87, pp. 289-291 (1986)]. Moreover, the cis isomer of urocanic acid is released from irradiated mouse skin, presumably a photoproduct of the trans isomer, normally present in the skin [De Fabo et al., J. Exp. Med., 157, pp. 84-98 (1983)]. Ultraviolet photoproducts of purified urocanic acid also were able to suppress DH to herpes virus in mice [Ross et al., J. Invest. Dermatol., 87, pp. 630-633 (1986)], so there may be more than one inducer or more than one cutaneous step in this process. Neither the mechanism of action, nor the source of the active substance, has been identified with certainty. Also, it is now known what normal physiological function, if any, is served by the suppressor cells. These cells, however, prevent rejection of tumor tissue, thus allowing ultraviolet carcinogenesis [Fisher et al., Science, 216, pp. 1133-1134 (1981)].

It is obvious that ultraviolet radiation suppression of delayed hypersensitivity can prevent rejection of ultraviolet radiation exposed skin, at the risk of the long-term consequence of elevated skin tumor susceptibility. It would be advantageous to eliminate this effect in order to reduce or eliminate the possible long-term consequence of skin cancer in individuals who have sustained recent sun exposure.

An opposite result and corresponding problem exist in the instance of percutaneous drug delivery systems. For example, numerous agents that are desirably administered topically for the benefits of enhanced speed of administration have been discouraged due to the adverse side effects resulting from the adverse reaction of the skin to contact with these agents. Such materials include common drugs such as the penicillins, nitroglycerine, scopolamine, Nystatin, and others, which elicit an allergic dermatitits resulting either directly from the administration of the drug or from the vehicle in which the drug is exposed. For example, the disk variety of transdermal delivery system manufactured by G. D. Seale, Inc. elicits an adverse dermatitis resulting from the contact between the silicone adhesive and the skin. Similarly, a transdermal delivery system for nitroglycerine including propylene glycol as a part of the vehicle has elicited problems of hypersensitivity to this specific ingredient.

In this context, investigation has been initiated of certain steroid compounds to determine whether these would have a favorable effect of modulating delayed hypersensitivity appropriately to favorably address the foregoing diverse situations. The inventors herein investigated certain glucocorticoid compounds such as triamcinolone acetonide, while exhibiting certain suppressive effects upon delayed hypersensitivity, also exhibited an adverse systemic effect which rendered it undesirable as a candidate for inclusion in situations where suppression of delayed hypersensitivity is desirable. Similarly, in work performed by the present inventors and embodied in parent application Ser. No. 030,764, the disclosure of which is incorporated herein by reference, the 21-oic methyl ester of triamcinolone acetonide (TA) or TAme was found to inhibit the ultraviolet-induced suppression of delayed hypersensitivity. In the present disclosure, this same group of compounds i.e. the glucocorticoid carboxylic acid esters were further investigated and have been found to truly serve as modulators of cutaneous delayed hypersensitivity, in that, they can be co-administered with otherwise reaction-provoking compounds and will suppress delayed hypersensitivity in a highly localized manner, thus obviating the danger of adverse systemic or cutaneous effects. They can additionally be utilized in the treatment of certain disease states where a highly localized effect on the cellular immune responses in the skin is desired.

SUMMARY OF THE INVENTION

In accordance with the present invention, glucocorticoid carboxylic acid esters, and more particularly glucocorticoid carboxylic alkyl esters have been determined to exhibit a modulating effect upon cutaneous delayed hypersensitivity. Thus, the present invention includes compositions for the inhibition of ultraviolet radiation suppression of delayed hypersensitivity, for the purpose of reducing the incidence of the development of skin cancer and compositions for the inhibition of the sensitization and elicitation phases in contact hypersensitivity. Likewise, similar compositions for topical administration may be prepared comprising a glucocorticoid carboxylic acid ester in combination with one or more drugs capable of topical or percutaneous administration, which drugs exhibit by themselves an arousal of cutaneous delayed hypersensitivity. Particular compositions may be prepared in ointment, gel or spray form with conventional ingredients such as carriers, pH stabilizers and the like for topical administration.

In a further embodiment of the present invention, percutaneous drug delivery systems in the form of transdermal patches and the like may be prepared wherein the active ingredient or drug to be delivered is admixed in combination with the glucocorticoid carboxylic acid esters of the present invention in an amount sufficient to suppress delayed hypersensitivity caused by one or more of the ingredients of the percutaneous delivery system. The glucocorticoid carboxylic esters of the present invention may be embodied into each of the transdermal delivery systems including the disk system, the gel system and the layer system, all of which are well known in the art.

In the instance where the glucocorticoid carboxylic acid ester of the present invention to be incorporated into creams, gels, ointments and sprays, an effective amount of same is that concentration sufficient to yield a skin dose of from 1 to 100 micrograms per $cm^2$ per application. In the instance where transdermal delivery systems using time-controlled delivery are involved, the dosage range of the glucocorticoid carboxylic acid esters of the present invention should be approximately 100 micrograms per 24 hours of activity.

Additionally, the glucocorticoid carboxylic acid esters of the present invention can be incorporated into a gel or paste of "spansule" or other delayed-release formulation which can be administered by injection. Such formulations can be utilized to treat internal inflammatory diseases, e.g. rheumatoid arthritis, intractable buritis, osteogenic arthritis, and certain internal inflammatory neurological disorders, such as multiple sclerosis, amyotrophic lateral sclerosis, and myathenia gravis, which could not be treated with convention steroids due to systemic side effects. Typically, the formulations will contain the active glucocorticoid carboxylic acid ester in an amount 0.005 to 1.0 percent by weight, and preferably 0.01 to 0.2 percent by weight.

The glucocorticoid carboxylic acid esters of the present invention are easily incorporated into all of the aforementioned products with conventional processing and need only pH stabilization ear neutrality in view of the steroidal structure. Products containing these glucocorticoid carboxylic acid esters achieve unexpected improvements in administration and delivery of drugs without the harmful side effects normally experienced with steroids. Also, the compounds of the present invention employed as the sole active ingredient of topical compositions can serve to effectively treat the adverse effects of excessive exposure to ultraviolet radiation by encouraging the onset of delayed hypersensitivity and thereby reducing the incidence of the development of skin cancer. Additionally, the topical compositions containing only the compounds of the present invention can be utilized in the treatment of disease states of for the inhibition of the sensitization and elicitation phases in contact hypersensitivity.

Accordingly, it is a principal object of the present invention to prepare compositions for topical application which are capable of selectively modulating cutaneous delayed hypersensitivity without exerting undesirable systemic effects.

It is a further object of the present invention to prepare compositions as aforesaid which can suppress delayed hypersensitivity to facilitate the administration of therapeutic compounds or their carriers that individually elicit undesirable percutaneous delayed hypersensitivity.

It is a further object of the present invention to provide compositions as aforesaid which may be administered to favorably inhibit the ultraviolet radiation suppression of delayed hypersensitivity to correspondingly reduce the incidence of the development of skin cancer.

It is a still further object of the present invention to prepare transdermal drug delivery systems embodying the compositions as aforesaid.

Other objects and advantages will become apparent to those skilled in the art from a review of the ensuing detailed description.

BRIEF DESCRIPTION OF THE DRAWINGS

The FIGURE is a graphical presentation of data illustrating the effect of a glucocorticoid carboxylic acid ester on the sensitization and response to challenge elicited from skin by the application of the known allergen DNCB.

DETAILED DESCRIPTION OF THE INVENTION

In accordance with the present invention steroid-based modulators of cutaneous delayed hypersensitivity have been discovered which can exert essentially opposite affect on delayed hypersensitivity to achieve a broad range of beneficial results. More particularly, a class of steroid-based compounds comprising the glucocorticoid carboxylic acid esters such as the 21-oic acid methyl ester of triamcinolone acetonide (Tame) may be prepared in a variety of topical compositions and may be included in transdermal or percutaneous drug delivery systems.

The glucocorticoid carboxylic acid esters of the present invention may be prepared individually in a variety of topical compositions wherein they constitute the primary active ingredient thereof, for the purpose of the administration of such compositions to inhibit the ultraviolet induced suppression of cutaneous delayed hypersensitivity. For example, a particular glucocorticoid carboxylic ester discussed hereinafter by way of example but not by way of limitation is the 21-oic methyl ester of triamcinolone acetonide. This ester and the remaining esters of the present invention can be conveniently prepared by the synthetic routes detailed in Gorsline et al., *Endocrinology*, 116, pp. 263–273 (1985).

The glucocorticoid carboxylic acid esters can be utilized in the method of the present invention alone, or more conveniently, formulated into topical compositions suitable for dermatological use. Such formulations may for example, comprise the glucocorticoid carboxylic acid ester ester in a vehicle suitable for topical administration to the epidermis of an individual in need of therapy for exposure to ultraviolet radiation or sunburn.

Such topical compositions are exemplified by ointments, creams, lotions, aerosols, gels or soaps. These compositions will normally be based upon standard dermatological carriers which are pharmaceutically acceptable and cosmetically elegant, such as those selected from pharmaceutically acceptable polyalkylene glycols, isopropanol, gelatin, benzyl alcohol, gums, glycerol and petrolatum. Optionally, the compositions may contain preservatives, aerosol propellants, such as hydrocarbons, and coloring, thickening, suspending, dispersing, emulsifying, wetting, stabilizing and buffering agents. These formulations are envisioned to contain the glucocorticoid carboxylic acid methyl ester in an amount of from about 0.005 to 1.0% by weight, with a range of form about 0.01 to 0.2% by weight being preferable for topical application.

The compositions of the present invention containing the glucocorticoid carboxylic acid ester are utilized to treat the epidermix of individuals who have been exposed to ultraviolet radiation in potentially carcinogenic quantities. The amount of such exposure may vary from individual to individual and it is envisioned that a physician or other treatment administrator will consider factors such as the individual's age, weight, complexion and degree of exposure in administering the proper dosage. Treatment is envisioned to be accomplished by applying the topical composition to completely cover the affected area The dosage of the glucocorticoid carboxylic acid ester is preferably in the range of 0.01 mg/m$^2$ to about 100 mg/m$^2$ skin surface area. The predicted frequency of application is once or twice daily, but this may of course be varied depending upon the particular individual involved.

Thus, the method of treatment utilizing the glucocorticoid carboxylic acid ester of the invention to treat individuals exposed to ultraviolet radiation comprises administering the ester or a topical composition thereof to an individual in need of such therapy in an amount sufficient to inhibit the ultraviolet radiation suppression of delayed hypersensitivity in the epidermis thereby reducing or obviating the carcinogenic effects of the ultraviolet radiation.

The unique properties of the active ingredient, allow treatment of the epidermis exposed to ultraviolet radiation without concomitant systemic effects. Since this steroid acts only upon the epidermis, it is uniquely suited to the method of treatment of the present invention.

Treatment of the epidermis of individuals suffering from ultraviolet radiation exposure (sunburn) the method of the present invention will inhibit the ultraviolet suppression of delayed hypersensitivity in the epidermis. Thus, for example, the administration of the triamcinolone acetonide 21-oic methyl ester will prevent the induction of suppressor T lymphocytes which lymphocytes are responsible for the prevention of rejection of tumor tissue. By prevention of such a response, the epidermis will thus continue in a normal fashion which would thus allow the rejection of tumor tissue and prevent the carcinogenic effects of the ultraviolet radiation exposure. The elicited response to treatment with triamcinolone acetonide 21-oic acid methyl ester in the individual's epidermis will be rejection of the sunburned skin. This rejection will result in intense infiltration, hyperproliferation and purulent crusting in the epidermis of the individual. This is a manifestation of a normal immune system which is indicative of the fact that the ultraviolet radiation suppression of delayed hypersensitivity has been successfully blocked. Thus, the so-treated individual will have increased his chances of rejecting neoplasm and thus reduce or obviate his chances of sustaining ultraviolet radiation carcinogenesis.

The compositions of the present invention containing the glucocorticoid carboxylic acid ester can additionally be utilized in the treatment of patients suffering from polymorphic light eruption (PLE) and related conditions. PLE is a complex of diseases which are characterized by delayed, immunological reaction to ultraviolet light in the wavelength range that is not phototoxic. The prevalence is about 10% in caucasians and less in dark-skinned individuals. Variations of the disease include Hutchinson's prurigo aestivale. The reactions commonly involve massive infiltration by T-lymphocytes. Typical glucocorticoid therapy is not recommended because of the severe side effects (Bernhard, et. al., "Fitzpatricks'Dermatology in General Medicine," Chapter 129, pp. 1481–1503, McGraw-Hill Pub.). Due to the ability of the glucocorticoid carboxylic acid esters of the present invention to prevent the induction of the T-lymphocytes, the glucocorticoid carboxylic acid esters of the present invention can be utilized to successfully treat PLE and related conditions involving the same mechanism of action by preventing the induction of the T-lymphocytes.

In a further embodiment of the present invention, patients suffering from xeroderma pigmentosum can be treated with an amount of a glucocorticoid carboxylic acid ester sufficient to inhibit the cellular immune response to the nascent tumor after accidental UV exposure to inhibit tumor formation in the patient. Xeroderma pigmentosum is a genetic disease characterized by a photosensitivity which usually results in afflicted individuals developing multiple skin cancers. Topical administration of the esters of the present invention in any of the above-described compositions produces the desired effects.

As indicated earlier, the glucocorticoid carboxylic acid esters of the present invention also possess the ability to suppress cutaneous delayed hypersensitivity in the instance where they are administered in conjunction with agents which otherwise elicit such response. As will be apparent from the data presented in the Examples that follow, tests wherein the compound 1-chloro-2,4-dinitrobenzene (DNCB), a known powerful allergen was co-administered with the glucocorticoid carboxylic acid esters of the present invention, the delayed hypersensitivity normally evoked by DNCB was prevented. Similarly, in the instance where a challenge dose of DNCB was applied at a site distal from the site of sensitization in previously sensitized animals in conjunction with the present glucocorticoid carboxylic acid esters, the elicitation or expression of delayed hypersensitivity was again blocked. Accordingly, compositions for topical administration of active pharmaceutical compositions that otherwise elicit allergic reaction can be facilitated by the inclusion in such compositions of an effective amount of the glucocorticoid carboxylic acid esters of the present invention.

The glucocorticoid carboxylic acid esters may include the alkyl esters thereof, of which TAme is exemplary only of 21-oic acid esters. Steroids having the acid moiety at other positions such as the 16-oic acid esters have likewise been established to be effective in this regard and are thereby included in accordance with the present invention. Suitable glucocorticoid carboxylic acid esters contemplated in accordance with the present invention include triamcinolone acetonide 21-oic methyl ester; Methyl 11β,17α-Dihydroxy-3,20-dioxo-1,4-pregnadiene-21-oate; Methyl 11β-hydroxy-3,20-dioxo-1,4-pregnadiene-21-oate; Methyl 11β, 17,20α-Trihydroxy-3-oxo-1,4-pregnadiene-21-oate; Methyl 11β,17,20α-Trihydroxy-3-oxo-1,4-pregnadiene-21-oate; Methyl 11β-Hydroxy-17α,20α-isopropylidenedioxy-3-oxo-1,4-pregnadiene-21-oate; Methyl 11β-Hydroxy-17α,20β-isopropylidenedioxy-3-oxo-1,4-pregnadiene-21-oate; 11β, 17,20α-Trihydroxy-3-oxo-1,4-pregnadiene-21-N-(n-propyl)carboxamide; 11β,17,20α-Trihydroxy-3-oxo-1,4-pregnadiene-21-N-(n-propyl)-carboxamide; Methyl 11β,17α,21-Trihydroxy-3,20-dioxo-1,4-pregnadiene-16-carboxylate; Methyl 11β,21-Dihydroxy-3,20-dioxo-1,4-pregnadiene-16-carboxylate; and Methyl 9α-fluoro-11β-hydroxy-16,17α-isopropylidenedioxy-1,4-pregnadiene-21-oate. The above compounds are merely illustrative and not restrictive as other esters of similar structure may be utilized herein.

As in the instance where the composition may be prepared for the treatment of sunburn, compositions for topical application of materials which otherwise elicit the immune response of delayed hypersensitivity may be prepared which would include the conventional ingredients of such composition with the addition of the glucocorticoid carboxylic acid esters of the present invention. For example, compositions being directly topically applied, such as ointments, creams, gels and sprays may contain the glucocorticoid carboxylic acid esters of the present invention in an amount and concentration sufficient in yield a skin dose of 1 to 100 microgram per cm$^2$ per application. In the instance where products such as time-release drug delivery systems are concerned, the dosage of the present glucocorticoid should range to approximately 100 micrograms per 24 hours of delivery. As with the compositions for direct application to the skin, the compositions prepared for the time release devices should be otherwise conventional in amount and method of preparation with the addition that the glucocorticoid carboxylic acid esters of the present invention should be included in the same fashion as with the active ingredient of the composition or device. The only qualification to be observed in the preparation of compositions containing the glucocorticoid carboxylic acid of the present invention is that the pH of the resulting composition should be maintained as closely to neutrality as possible to prevent any degradation of the glucocorticoid. This accounts for the pH sensitivity of these steroid-based compounds.

The administration of the compositions and products including the glucocorticoid carboxylic acid esters of the present invention is no different than that which would be followed for these products under conventional circumstances, and further disclosure with respect to periodicity, strength and like parameters of administration is accordingly not presented. This is so, as the characteristics of the glucocorticoid carboxylic acid esters of the present invention facilitate such freedom of operation, in view of the fact that these steroids exhibit no adverse systemic effects, but merely act locally when applied in topical fashion as provided herein.

The following examples describe in detail the methods and compositions illustrative of the present invention. It will be apparent to those skilled in the art that many modifications, both of materials and methods, may be practiced without departing from the purpose and intent of this disclosure.

EXAMPLE I

Materials: Mice aged about 4 months are secured from the Rockefeller University colony established in December, 1983, from NIH Balb/CAnN stock. DNCB (1-chloro-2,4-dinitrobenzene) and TA (triamcinoone acetonide) are purchased from Sigma; TAme (triamcinolone acetonide 21-oic methyl ester) is synthesized as described by Gorsline, Bradlow and Sherman [*Endocrinology*, 116, pp. 263–273 (1985)].

Irradiation: To handle the irradiation of mice in groups, holes 2 cm on a side are cut in a cardboard mask which is then set above a bank of two GEG15T8 high pressure Hg lamps emitting primarily at 254 nm. This lamp minimizes possible systemic effects of irradiation. 254 nm light penetrates the epidermis less deeply than sunlamp radiation, which is more commonly used to study UV suppression of delayed hypersensitivity. Incident dose is 12 W/m$^2$ as measured by an actinometrically calibrated Black Ray model J-225 shortwave UV monitor. Mice anesthetized with nembutal injected i.p., 2 mg/kg in 0.5 ml saline, are fastened gently to the mask with tape for the 30–40 minute exposure. The cumulative exposure, 6 J/cm$^2$ (total 24 J per mouse), is applied from below the mask to clipper-shaved skin on the lower abdomen.

Steroid treatment: Forty micrograms of TA or TAme, dissolved at a concentration of 0.2% in absolute UPS ethanol, is spread over the UV-irradiated site and spread with a microliter pipette (Rainin Pipetman P-20); the same dosage being used for both compounds since they differ only by a methyl group. (TA is used to compare results with a glucocorticoid having undesirable systemic effects).

DNCB Applications: Animals are shaved on the lower back to expose about 4 cm$^2$ skin. For experimental sensitization, 20 microliters of a 2% solution of DNCB in ethanol are applied to this shaved site. To ascertain the degree of delayed hypersensitivity; four days after the first sensitizing application, 5 microliters of DNCB freshly dissolved to 2% in ethanol are applied to the inner and outer aspects of each animal's left ear (total 200 micrograms). Ear thickness is measured just prior to this challenge and at 24 hour intervals thereafter with the aid of a dissecting microscope and a dial engineer's caliper.

Histology: Abdominal skin, fixed in formalin, is embedded in paraffin; microtome sections are taken and stained with hemaxtoxylin-eosin.

Procedure: Male mice from a colony are caged in six groups. Three of the groups of mice are exposed to 4 kJ/m$^2$ 254 nm light; others are shaved but not irradiated. Immediately following ultraviolet exposure (day 0), mice are painted with steroid or with vehicle (ethanol) at the site of irradiation. This treatment is repeated 3 times at approximately 24 hour intervals, then discontinued. On day 5, the lower back of each animal is shaved to expose about 4 cm$^2$ skin. Animals to be sensitized are painted at this site with 1-chloro-2,4-dinitrobenzene (DNCB) in ethanol, and this treatment is repeated 24 hours later (day 6). The test for delayed hypersensitivity response is maximal four days after the first sensitizing treatment (not shown). Day 9 is chosen to challenge for contact sensitivity by application to the left ear of 1-chloro-2,4-dinitrobenzene in ethanol. Ear swelling is measurable on day 10, but it peaks on day 11, 48 hours following challenge.

The data for this experiment are summarized in Table I, where the average for each group of mice is shown as the ratio of left and right ear thicknesses. The average thickness of the left and right ears for most groups was 0.24 mm on day 9. The sensitization causes the 1-chloro-2,4-dinitrobenzene treated skin to thicken and become indurated. This response is most pronounced in the controls, the TAme only, and the ultraviolet radiation +TAme groups.

Following challenge, ears swell according to group. The swelling is accompanied by a mild erythema, and a visual estimate of the extent of the erythema and swelling correlates well with the caliper measurements: Ears of sensitized controls swell to about twice their normal thickness. Ears of unsensitized mice do not swell. The response measured here is therefore a consequence of delayed hypersensitivity rather than primary irritation, which, at higher 1-chloro-2,4-dinitrobenzene concentrations than those used here, also produces ear swelling. For instance, 1-chloro-2,4-dinitrobenzene irritation is measurable in the controls.

The ultraviolet suppression of sensitization is readily apparent when columns 3 and 4 of Table I are compared for the sensitized control and ultraviolet radiation only groups. Ultraviolet radiation on day 0 suppressed the swelling for all but one animal in which the response was delayed but about normal in magnitude. In sharp contrast, mice treated with TAme either following ultraviolet radiation or without ultraviolet radiation responded like the control mice, showing normal delayed hypersensitivity. This shows that treatment with TAme immediately following ultraviolet irradiation prevents ultraviolet radiation suppression of delayed hypersensitivity.

Mice that were treated with triamcinolone acetonide after ultraviolet radiation like those treated with triamcinolone acetonide alone on days 1-3, had ears 0.18 mm thick on day 9, about 0.06 mm thinner than those of other mice. When the right ear is taken as the baseline, the triamcinolone acetonide only group was strongly suppressed for delayed hypersensitivity. The UV+TA group exhibited a weak degree of delayed hypersensitivity comparable to that in the UV only group. Mice treated with triamcinolone acetonide 21-oic acid methyl ester but not with UV, on the other hand, exhibited normal delayed hypersensitivity. Triamcinolone acetonide gains access to the circulation and thus may act at a distance. In this experiment, triamcinolone acetonide could act at the spleen or at the skin to prevent delayed hypersensitivity. Testing for the effect of TAme on delayed hypersensitivity at the site of sensitization is as follows: On day 0, the shaved back skin of C57B1/K6S mice are painted with 1-chloro-2,4-dinitrobenzene; with TAme; or with both compounds. On day 6, the animals are tested for delayed hypersensitivity by application of 1-chloro-2,4-dinitrobenzene or of TAme +DNCB. The data obtained shows that TAme prevents delayed hypersensitivity when applied to the back at the time of sensitization and also prevents ear swelling when applied to the ear at the time of challenge.

Some animals of the experiment shown in Table I are killed on day 3 or 12 for histological examination of the UV-exposed portion of their abdominal skin. The evaluation is summarized in Table II. The skin of UV only mice on day 3 contained a diffuse dermal infiltrate, consisting of about 90% neutrophils and 10% monocytes and macrophages. The inflammatory changes were not accompanied by erythema and were in other ways characteristic of UV-exposed mouse skin [*Photobiol.* 37, pp 623–631 (1983)]. The dermis of TAme-treated, UV-irradiated mice was infiltrated by polymorphonuclear leukocytes. Macroscopically, there was induration and purulent crusting. The infiltrate persisted for at least 12 days in the TAme plus UV-treated mice, when it had subsided in the ultraviolet radiation only group. There was no apparent influx or mononuclear cells in the UV+TAme infiltrate, suggesting that the cellular immune system was unresponsive to the ultraviolet radiation damaged skin. The other striking histological finding in UV+TAme treated animals was the intense epidermal hyperplasia, accompanied by acanthosis and hyperkeratosis. In many places, the epidermal thickness exceeded 20 nucleated cells. Normal mouse belly skin is 1-3 nucleated cells thick. This prolonged, exaggerated response was not noted in the ultraviolet radiation only group, or in the triamcinolone acetonide 21-oic acid methyl ester only group, so it is the result of an interaction of the two treatments. The triamcinolone acetonide 21-oic acid methyl ester only group, in contrast, had a normal epidermis, accompanied by mild follicular hyperplasia.

TABLE I

| GROUP | DAY | Group average ear thickness (hundredths of a millimeter) | | | | |
|---|---|---|---|---|---|---|
| | | left (test) | std | right (control) | std | 1/r | 1 − r |
| Sensitized control | 9 | 24.2 | 1.3 | 24.4 | 1.4 | 0.99 | −0.20 |
| | 10 | 42.6 | 3.6 | 26.9 | 1.5 | 1.58 | 15.6 |
| | 11 | 48.8 | 2.0 | 26.4 | 1.2 | 1.84 | 22.4 |
| UV only | 9 | 23.9 | 1.4 | 25 | 0.9 | 0.95 | −1.0 |
| | 10 | 32.0 | 1.3 | 28.2 | 1.5 | 1.13 | 3.83 |
| | 11 | 37 | 2.0 | 30 | 1.7 | 1.23 | 7 |
| TAme only | 9 | 25.5 | 3.1 | 24.8 | 0.7 | 1.02 | 0.66 |
| | 10 | 41.3 | 2.2 | 23.6 | 2.3 | 1.74 | 17.6 |
| | 11 | 45.1 | 3.8 | 2.48 | 1.1 | 1.81 | 20.3 |
| TA only | 9 | 18.6 | 2.4 | 17.5 | 2.5 | 1.06 | 1.16 |
| | 10 | 33.3 | 2 | 22.5 | 2 | 1.48 | 10.8 |
| | 11 | 26.1 | 1.1 | 22.5 | 2.0 | 1.16 | 3.66 |
| UV + TAme | 9 | 24.7 | 1.3 | 24.5 | 1.2 | 1.00 | 0.2 |
| | 10 | 42.4 | 2.2 | 26.6 | 1.0 | 1.59 | 15.7 |
| | 11 | 45.2 | 2.7 | 25 | 0.9 | 1.81 | 20.2 |
| UV + TA | 9 | 17.6 | 1.8 | 16.4 | 1.7 | 1.07 | 1.2 |
| | 10 | 29.6 | 1.7 | 22.6 | 1.5 | 1.30 | 7 |
| | 11 | 31.4 | 2.1 | 21.4 | 1.5 | 1.46 | 10 |
| Unsensitized control | 9 | 25.4 | 0.8 | 25.8 | 2.3 | 0.98 | −0.4 |
| | 10 | 27.1 | 1.6 | 26.7 | 1.8 | 1.01 | 0.41 |
| | 11 | 27.5 | 0.7 | 27.6 | 1.4 | 0.99 | −0.0 |

TABLE II

SUMMMARY OF HISTOLOGICAL DATA

| | Day 3 | | | | Day 12 | | | | |
|---|---|---|---|---|---|---|---|---|---|
| | S | Tm | Tm+UV | UV | Tm | TA | TA+UV | Tm+UV | UV |
| INFLAMMATORY CHANGES | | | | | | | | | |
| Spongiosis | | | +++ | + | | | ++ | | |
| Infiltrate Neutrophilic | | | | | | | | | |
| Dermal | | | ++ | ++ | | | ++ | | |
| Epidermal | | | ++ | | | | ++ | | |
| Mononuclear | + | | | + | | | | | |
| HYPERPLASTIC CHANGES | | | | | | | | | |
| Dermel Epidermal | | | | | | | + | | |
| Hyperkeratosis | + | + | | + | | + | +++ | + | |
| Hypergranulosis | | | | + | | | +++ | + | |
| Acanthosis | | | | | | | +++ | | |
| ATROPHIC CHANGES | | | | | | | | | |
| Dermal | | | | | | ++ | ++ | | |
| Epidermal | | | | | | ++ | | | |
| NECROSIS | | | ++ | ++ | | | + | | |

KEY
S = shaved control
Tm = triamcinolone acetonide 21-oic acid methyl ester
TA = triamcinolone acetonide
UV = ultraviolet radiation

EXAMPLE 2

In this Example, the effect of the glucocorticoid carboxylic acid ester TAme on the sensitization and response to challenge with DNCB was investigated. Accordingly, sixteen male and female C57Bl/K6S mice aged 10–14 weeks were shaved to expose their lower back skin and divided into four groups. Solutions containing 0.2% DNCB or 0.2% each DNCB and TAme were prepared in a mixture of 90% ethanol and 10% sesame oil, and the phases were mixed by gentle heating and shaking. The lower back of each animal was smeared with 100 microliters of one of the above mixtures, or with 100 microliters of vehicle alone on day zero. Animals receiving TAme on day zero received it again on days 1 through 3, while other animals received vehicle only. On day 5 the left ear of each animal was painted with 20 microliters of DNCB at 0.1% in acetone, with or without 0.2% TAme. Ear thickness was measured on day 7, and the average of three measurements for each animal was used to calculate the group average which is shown in the FIGURE.

Referring to the FIGURE, data are for the ratio of the thickness of the left and right ears of 4 mice in each group. Error bars represent the standard deviation for the entire set of measurements. (boxes): DNCB only at both sensitization and challenge; (circles): DNCB at challenge only, to test for DNCB irritation; (triangles): DNCB at sensitization and challenge, TAme at sensitization; (diamonds): DNCB at sensitization and challenge, TAme at challenge only.

The date in the FIGURE show that TAme prevented DH when applied to the back at the time of sensitization and also prevented ear swelling when applied to the ear at the time of challenge. This indicates that the main inhibitory effect of TA in the previous experiment was due to the systemic absorption of the drug, rather than an effect at the skin. The data of the FIGURE also show that TAme, though lacking in systemic effects, effectively prevented DH either when applied together with DNCB at the time of sensitization, or when applied conjointly with the DNCB at the time of challenge.

EXAMPLE III

To further test the theory that other glucocorticoids might affect sensitization both at the site of application and by systemic action, the following experiment was performed with the topical glucocorticoids Beclomethasone and Budesonide as well as with TAme and TA, TAme alone representing the glucocorticoid of the invention. Like TA, but unlike TAme, Beclomethasone and Budesonide are metabolized slowly by serum and liver enzymes.

Mice were sensitized on their backs, and glucocorticoid was applied either with the DNCB at the site of sensitization (B groups animals) or to a distal site (the abdomen; (A group animals). Glucocorticoid treatment was continued on days 1–3. On day 5, two mice from each group were bled just prior to challenge to test for circulating B (17-desoxycortisol). B is the predominant circulating glucocorticoid of mice. Ear thickness was measured, and there were not significant differences between the groups. The mice were then challenged, and ear thickness was measured again on day 7. Data for B and for the averaged ratio and difference of left and right ear thicknesses are shown in Table III below, as a percent of the negative control (Control- group).

The data show that Budesonide, Beclomethasone, and TA all suppressed plasma B at least 10-fold, whereas TAme had no effect. The drugs that suppressed plasma B also abolished DH, there being no statistically significant difference between these data and the negative controls. The suppression of DH was similar in magnitude whether the drug was applied to the abdomen or to the back. TAme, on the other hand, had no effect on DH when applied to the abdomen; in fact there was an apparent stimulation as compared to the positive control. However, TAme applied to the back prevented development of DH. The effect was less than that of the other glucocorticoids, but the data were not statistically different from the negative controls. Thin layer chromatography of the various mixtures held for 2 days at 37° C. revealed no evidence for chemical reactivity between the glucocorticoids and DNCB (not shown). The data show that glucocorticoids can prevent sensitization at the site of application of DNCB or at a distal site, but in the latter case, only if they are able to penetrate the epidermis in an active form and act systemically. Importantly, however this data illustrates that TAme does inhibit DH caused by DNCB but does not act systemically, in contrast with the other known glucocorticoids.

TABLE III

Effect of Glucocortiocids on Sensitization to DNCB

|  | Control | Beclomethasone | | Budesonide | | TA | | TAme | | Control+ |
|---|---|---|---|---|---|---|---|---|---|---|
| DNCB | — | + | + | + | + | + | + | + | + | + |
| Steroid | — | A | B | A | B | A | B | A | B | — |
| B level | 12.7 | 0.61 | 1.25 | 0.2 | 0.0 | 0.14 | 0.0 | 11.3 | 14.9 | 6.2 |
| Mean L/R Day 7 | 100 | 104 | 101 | 100 | 104 | 101 | 103 | 172‡ | 123□‡ | 143○ ‡‡ |
| Mean L-R Day 7 | 100 | 154 | 177 | 97 | 168 | 160 | 297 | 1380** | 383Δ† | 808+Δ• |

‡$P_{1-8} < 0.001$; ○$P_{1-10} < 0.06$; □$P_{1-9}$ NS; ‡‡$P_{9-10}$ NS
*$P_{1-8} < 0.0005$; +$P_{1-10} < 0.03$; †$P_{1-9}$ NS; •$P_{8-10} < 0.06$; Δ$P_{9-10}$ NS
All other cases were not significantly different from the control value.
B values μg/mL;
DNCB 200 μg as sensitization dose; 50 μg as challenge dose
Glucocortioids 20 μg per application
B = steroid applied on the back, A = steroid applied to the abdomen The following examples are presented to illustrate particular formulations where in the glucocorticoid carboxylic acid esters of the invention are incorporated into various products for topical application.

| EXAMPLE IV | |
|---|---|
| Cream Formulation | mg/g |
| Triamcinolone acetonide 21-oic acid methyl ester | 0.5 |
| Cetyl Esters Wax | 20.0 |
| Cetyl Stearyl Alcohol | 100.0 |
| Sorbitan Monostearate | 25.0 |
| Polysorbitan 60 | 20.0 |
| Cetyl Dodecanol | 100.0 |
| Propylene Glycol | 100.0 |
| Benzyl Alcohol | 10.0 |
| Purified Water | To make 1 g |

| Example V | |
|---|---|
| Cream Formulation | mg/g |
| Triamcinolone acetonide 21-oic acid methyl ester | 2.0 |
| Stearic Acid | 60.0 |
| Propylene Glycol Monostearate | 100.0 |
| Isopropyl myristate | 50.0 |
| Propylene Glycol | 100.0 |
| Polyoxyethylene 20 Sorbitan Monopalmitate | 60.0 |
| Methylparaben | 1.0 |
| Butylparaben | 4.0 |
| Purified Water | To make 1 g |

| Example VI | |
|---|---|
| Gel Formulation | mg/g |
| Triamcinolone acetonide 21-oic acid methyl ester | 1.0 |
| Propylene Glycol | 50.0 |
| Hydroxylppropyl Cellulose | 20.0 |
| Alcohol | To make 1 g |

| Example VII | |
|---|---|
| Gel Formulation | mg/g |
| Triamcinolone acetonide 21-oic acid methyl ester | 2.0 |
| Propylene Glycol | 350.0 |
| Alcohol | 350.0 |
| Carbomer 940 | 20.0 |
| Monoamylamine | 2.0 |
| Purified Water | To make 1 g |

| Example VII | |
|---|---|
| Lotion Formulation | mg/g |
| Triamincinolone acetonide 21-oic acid methyl ester | 1.0 |
| Ethyl Alcohol | 400.0 |
| Polyethylene Glycol 400 | 300.0 |
| Hydroxypropyl Cellulose | 5.0 |
| Propylene Glycol | To make 1 g |

This invention may be embodied in other forms or carried out in other ways without departing form the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of treating individuals suffering from xeroderma pigmentosum which comprises administering topically to the affected area of an individual in need of such therapy an effective amount of a glucocorticoid carboxylic acid ester sufficient to prevent skin cancer after exposure to UV radiation.

2. The method according to claim 1 wherein the glucocorticoid carboxylic acid ester is triamcinolone acetonide 21-oic acid methyl ester.

* * * * *